US00PP29461P3

(12) United States Plant Patent
Hansen

(10) Patent No.: US PP29,461 P3
(45) Date of Patent: Jul. 3, 2018

(54) ***LIGULARIA* PLANT NAMED 'KING KONG'**

(50) Latin Name: ***Ligularia* hybrid (L. dentate x hessei)**
Varietal Denomination: King Kong

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 123 days.

(21) Appl. No.: 14/999,485

(22) Filed: May 12, 2016

(65) Prior Publication Data

US 2017/0332540 P1 Nov. 16, 2017

(51) Int. Cl.
*A01H 5/02* (2018.01)

(52) U.S. Cl.
USPC ..... Plt./448
CPC ..... *A01H 5/025* (2013.01)

(58) Field of Classification Search
USPC ..... Plt./448
See application file for complete search history.

(56) References Cited

PUBLICATIONS

"Future Plants by Randy Stewart: *Ligularia*," http://rslandscapedesign.blogspot.com/search/label/Ligularia, Jun. 21, 2010, pp. 1-23.*

* cited by examiner

*Primary Examiner* — Anne Marie Grunberg

(57) ABSTRACT

The new and distinct cultivar of ornamental *ligularia* plant, *Ligularia* 'King Kong' with compact habit, vertical peduncle of dense clusters of large, upright, capitate, golden flowers on branched greyed-purple panicle. The shiny, magenta, orbicular to reniform leaves with coarsely serrated margins emerge from the ground on greyed-purple pubescent petioles and develop into a purplish dark-green by late summer flowering.

1 Drawing Sheet

Latin botanical classification: *Ligularia* hybrid; (*L. dentate* × *hessei*).

Variety denomination: 'King Kong'.

BACKGROUND OF THE INVENTION

The present invention relates to the new and distinct cultivar of *ligularia*, botanically known as *Ligularia* 'King Kong', and hereinafter referred to as the cultivar 'King Kong' or the "new plant". The new plant was discovered by the inventor at a wholesale perennial nursery in Zeeland, Mich., USA as a single selected seedling from seed of an isolation block of six herbicide-treated proprietary plants selected from *Ligularia* 'Britt-Marie Crawford' U.S. Plant Pat. No. 16,113 in the fall of 2009. The new plant was selected from many seedlings in evaluations beginning in 2011 and the individual selected seedling was originally assigned the breeder code H9-12-02. *Ligularia* 'King Kong' has been asexually propagated through division first in spring of 2012 at the same nursery in Zeeland, Mich. and subsequently also by sterile plant tissue culture. Plants of 'King Kong' have been found to be stable and identical to the original selection in multiple generations of asexual propagation.

No plants of *Ligularia* 'King Kong' have been sold, in this country or anywhere in the world, prior to the filing of this application, nor has any disclosure of the new plant been made prior to the filing of this application with the except that which was disclosed within one year of the filing of this application and was either derived directly or indirectly from the inventor.

'King Kong' has not been observed under all possible environments. The phenotype may vary slightly with different environmental conditions, such as temperature, light, fertility, moisture and maturity levels, but without any change in the genotype.

BRIEF SUMMARY OF THE PLANT

*Ligularia* 'King Kong' is unique from all other *Ligularia* known to the inventor. 'King Kong' compares most closely with its parent 'Britt-Marie Crawford' U.S. Plant Pat. No. 16,113. The plants of 'Britt-Marie Crawford' and 'King Kong' are very similar in habit, but the leaves of 'King Kong' are larger in width and length more reniform in leaf shape and more leaves in the clump have a darker pigment rather than the smaller, more rounded leaves with fewer leaves showing the darker pigment of 'Britt-Marie Crawford'. In comparison to 'The Rocket' (not patented) the new plant is about 30 cm smaller in height and width at flowering and has more purplish brown foliage. Compared to 'Little Rocket' U.S. Plant Pat. No. 14,621 the new plant is about the same height, but the foliage is larger and more purplish brown in color. 'Osiris Café Noir' U.S. Plant Pat. No. 21,351 has similar colored purplish brown foliage, but the foliage size is much smaller and foliage shape is ovate rather than the larger and orbicular to reniform foliage shape of 'King Kong'. 'Osiris Café Noir' and 'Osiris Fantaisie' U.S. Plant Pat. No. 19,302 both have ovate leaf blades that have deeply incised and undulating margins compared to the orbicular to reniform shape and coarsely dentate and flatter margins of 'King Kong'. 'Othello' (not patented) has smaller but similarly reniform leaf blades, and the blade and petiole coloration is not as dark brownish purple, and the leaf margins are not as coarsely serrated. 'The Rocket', 'Little Rocket' and 'Bottle Rocket' U.S. Plant Pat. No. 24,486 all have smaller flower heads in an unbranched raceme, whereas the larger flower heads of 'King Kong' are in a branched panicle.

The new plant, *Ligularia* 'King Kong', is distinct from all other *ligularia* known to the inventor through the following combined characteristics:

1. Vertical peduncle producing dense clusters of large, upright, capitate, golden flowers on branched panicle.
2. Dense rhizomes giving rise to compact shiny magenta leaves that become purplish dark-green by late summer flowering.
3. Orbicular to reniform leaf blade shaped with coarsely serrated margins.

BRIEF DESCRIPTION OF THE DRAWINGS

The photographs of the new plant demonstrate the unique traits and the overall appearance of *Ligularia* 'King Kong'. The colors are as accurate as reasonably possible with color reproductions. Variation in ambient light spectrum, source and direction may cause the appearance of minor variation in color. The plant used in the photographs was three years old and was grown in a nursery trial garden in Zeeland, Mich. with about 50% artificial shade and supplemental water and fertilizer when needed. No pinching or plant growth regulators have been used.

DETAILED BOTANICAL DESCRIPTION

Figure 1:
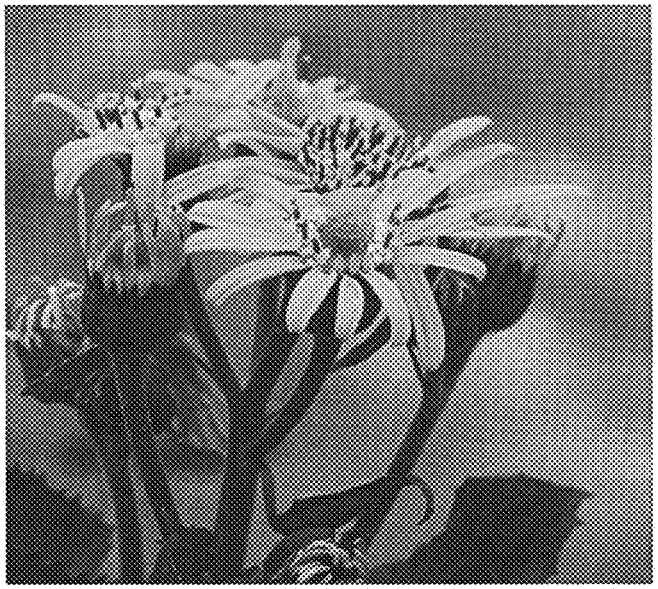
FIG. 1 shows a close-up of the flower scape.
Figure 2:
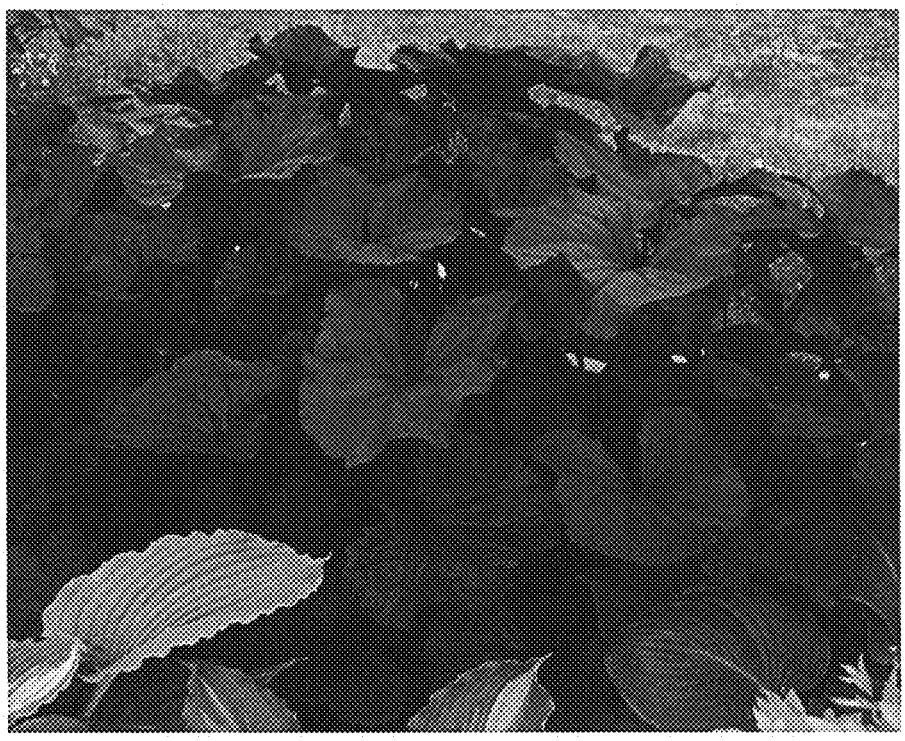
FIG. 2 shows the plant in early-season foliage color prior to flowering.

The following descriptions and color references are based on the 2001 edition of The Royal Horticultural Society Colour Chart except where common dictionary terms are used. *Ligularia* 'King Kong' has not been observed under all possible environments. The phenotype may vary slightly with different growing environments such as temperature, light, fertility, soil pH, moisture and plant maturity levels, but without any change in the genotype. The following observations and size descriptions are based on three-year-old plants growing in a 50% shaded trial garden in Zeeland, Mich. Plants were given supplemental water and fertilizer but no plant growth regulators were used.

Botanical classification: *Ligularia* hybrid;

Parentage: Female parent is from a block of herbicide-treated proprietary plants selected from *Ligularia* 'Britt-Marie Crawford'; male parent is presumed to be from the same block;

Plant habit: Hardy herbaceous perennial; rhizomatous, mounded foliage with flowers arranged on branched raceme just above foliage; foliage height to about 105 cm tall and flower height to about 120 cm tall; plant width about 100 cm at widest point at about 80 cm above soil level;

Growth rate: Moderately vigorous, finishing in a 65 mm plug from a rooted Stage 3 tissue culture explants in about 10 weeks and finishing in a 3.8 liter container from a 65 mm plug in about 7 weeks;

Root: Fine, fibrous; less than 0.5 mm diameter; heavily branched; color dependant on soil type, usually white to light cream with a tint of nearest RHS N186C;

Stem: About eight per plant; vertical; pubescent; about 120.0 cm long and about 17.0 mm diameter at base; primary branches to about 8.0 cm long and 5.0 mm diameter; angle of primary branches nearly tight against main peduncle; vertical;

Stem color: Mix of between RHS 187A and RHS 187B; with short white pubescence nearest RHS155C about 0.5 mm long;

Foliage: Glabrous; mostly acaulescent, with cauline leaves on raceme; about 20 per plant;

Leaf blade: Orbicular to reniform; coarsely dentate margin rounded apex, rarely subacute; cordate base with basal lobes nearly touching; laevigate both surfaces; total leaf blade to about 26.0 cm long and about 26.0 cm wide with basal lobes to about 14.0 cm long; average about 22.0 cm long and about 22.0 cm wide with basal lobes about 8.0 cm;

Leaf blade color: Emerging adaxial between RHS N77A and RHS N186C, abaxial nearest RHS N186C; at flowering abaxial surface nearest RHS 139A with blushing of nearest RHS N186C, abaxial blend between RHS 148C and RHS 152D with blushing of nearest RHS N186C;

Veins: Palmate; glabrous and impressed on adaxial surface and puberulent and ridged on abaxial surface;

Vein color: Emerging adaxial and abaxial between RHS N77A and RHS N186C; on mature leaves at flowering time primary adaxial veins nearest RHS 187A and secondary adaxial veins nearest RHS 148D; mature abaxial primary and secondary veins at flowering between RHS 187A and RHS 187B;

Petiole: Terete, puberulent, glaucous; about 60.0 cm long and about 8.0 mm diameter at base; petioles on cauline leaves shorter to about 18.0 cm and about 5.0 mm in diameter, diminishing in length distally;

Petiole color: Nearest RHS 187A;

Flower description:

Inflorescence: Capitate with ray and disc flowers arranged in branched panicle; average size flowering panicle about 15.0 cm long and about 14.0 cm across; about 12 to 15 flowers per branched panicle; with branches about 8.0 cm long and about 5.0 mm diameter containing 1 to 4 flowers per branch; flower timing in Michigan begins late summer and continues for about three weeks on the plant;

Buds about two days prior to petal opening: Oblong with rounded apex and rounded base; about 2.5 cm diameter and about 2.0 cm tall with petals curved around apex about 10.0 mm above disk;

Bud color: Phyllaries between RHS N186A and RHS N186B with exposed ray petals variable between both RHS 23A and RHS N25A;

Capitulum: Projected upwardly; actinomorphic; heterogamous; average size 6.0 cm across and 2.5 cm tall; average longevity on the plant, one week; self-cleaning; consisting of usually 12 to 15 outer ray florets and approximately 120 inner disk florets; receptacle size about 6.0 cm diameter and about 10.0 mm deep; fragrance has not been noted;

Ray floret: Average about 14 per capitulum; imperfect, pistillate.

*Ligule.*—One per flower; oblanceolate; margin entire; apex emarginate usually producing three lobes of unequal sizes with indentations about 2.0 mm and 1.0 mm deep; base cuneate; glaucous and glabrous both surfaces; attitude outward, distally arcuate slightly downward; about 2.8 cm long and 6.0 mm wide at middle, tapering to about 1.0 mm at base;

with typically two longitudinal ridges concave on adaxial and convex on abaxial.

*Ligule color*.—Adaxial between RHS 23B and RHS 23A, abaxial RHS 12D on abaxial side.

*Pistil*.—Single.

*Style*.—About 8.0 mm long and less than 0.5 mm diameter.

*Stigma*.—Split in two segments in distal 1.5 mm and with maturity curling around over 360 degrees; style and stigma color beginning nearest RHS 15B and maturing to nearest RHS 21A.

*Ovary color*.—Nearest RHS 144A.

Disk floret: About 120 per head arranged in center of receptacle; perfect; tubular;

*Corolla*.—Usually five, about 8.0 mm long and 1.0 mm diameter; fused into tube except distal 0.5 mm; acute apex; color nearest RHS 166A both surfaces.

*Androecium*.—Typically five linear anthers about 3.0 mm long and fused into tube around style; color nearest RHS N186C.

*Filament*.—Five, thin, about 3.0 mm long and less than 0.5 mm diameter.

*Pollen*.—Abundant color nearest RHS 17C.

*Pistil*.—Single.

*Style*.—About 8.0 mm long and less than 0.5 mm diameter.

*Stigma*.—Split in two segments in distal 1.5 mm and with maturity curling around over 360 degrees; style and stigma color beginning nearest RHS 15B and maturing to nearest RHS 21A.

*Ovary color*.—Nearest RHS N144A.

Pappus: Fine, numerous about 50 per seed; about 5.0 mm long and less than 0.1 mm diameter; color nearest RHS 161B at maturity;

Phyllaries: Linear; acute apex and base fused; margin entire; puberulent abaxial, glabrous adaxial; typically about 16 in two whorls; about 1.7 cm long and 4.5 mm wide; color between RHS 187A and RHS N187A;

Peduncle: About 5 per plant; terete; pubescent; attitude vertical; to about 120 cm long and 15.0 mm diameter at base, average about 105 cm long and 13.0 mm diameter; secondary branches to about 8.0 cm long and 5.0 mm diameter; angle of secondary branches tight against main peduncle;

Peduncle color: Mix of between RHS 187A and RHS 187B; with short white pubescence nearest RHS155C about 0.5 mm long;

Fruit terete: About 1.2 cm long and 1.5 mm diameter; with pappus at apex; color nearest RHS 200A;

Hardiness, pest and disease resistance: The new plant grows best with ample moisture, adequate drainage and shade from hot sun. Hardiness at least from USDA zone 4 through high temperatures of 36° Celsius. Disease and pest resistance beyond what is typical of that of other *Ligularia* has not been observed.

The invention claimed is:

1. A new and distinct cultivar of ornamental *ligularia* plant named *Ligularia* 'King Kong', as herein described and illustrated, suitable as a potted plant, cut flower, for the garden as a foliage and flower accent or en masse.

* * * * *